United States Patent
Wilson et al.

(10) Patent No.: US 10,195,608 B2
(45) Date of Patent: Feb. 5, 2019

(54) INTEGRATED POLYMER FOIL, PATCH-CLAMP ARRAY AND MEMBRANE VALVES

(71) Applicant: Sophion Bioscience A/S, Ballerup (DK)

(72) Inventors: Sandra Wilson, Birkerød (DK); Anders Brask, Frederiksberg (DK)

(73) Assignee: Sophion Bioscience A/S, Ballerup (DK)

( * ) Notice: Subject to any disclaimer, the term of this patent is extended or adjusted under 35 U.S.C. 154(b) by 43 days.

(21) Appl. No.: 15/120,948

(22) PCT Filed: Feb. 25, 2015

(86) PCT No.: PCT/EP2015/053893
§ 371 (c)(1),
(2) Date: Aug. 23, 2016

(87) PCT Pub. No.: WO2015/128352
PCT Pub. Date: Sep. 3, 2015

(65) Prior Publication Data
US 2016/0361717 A1  Dec. 15, 2016

(30) Foreign Application Priority Data
Feb. 25, 2014 (EP) ..................................... 14156499

(51) Int. Cl.
*B01L 3/00* (2006.01)
*G01N 33/487* (2006.01)

(52) U.S. Cl.
CPC ..... *B01L 3/502761* (2013.01); *B01L 3/50853* (2013.01); *B01L 3/502707* (2013.01);
(Continued)

(58) Field of Classification Search
CPC ....... B01L 2300/044; B01L 2400/0638; B01L 3/50853; B01L 3/502761; G01N 33/48728
See application file for complete search history.

(56) References Cited

U.S. PATENT DOCUMENTS

| 6,899,800 B2 | 5/2005 | Osipchuk |
| 2010/0028211 A1* | 2/2010 | Treptow .............. B01L 3/50853 422/400 |

FOREIGN PATENT DOCUMENTS

| DE | 102004038152 | 2/2006 |
| EP | 0093559 | 11/1983 |

(Continued)

OTHER PUBLICATIONS

Pfleging, W. et al, "Patterning of polystyrene by UV-laser radiation for the fabrication of devices for patch clamping", 2008 SPIE Digital Library—Subscriber Archive Copy, Proc. of SPIE vol. 6880 68800D-1, XP040433718, (Feb. 12, 2008).

*Primary Examiner* — Samuel P Siefke
(74) *Attorney, Agent, or Firm* — McHale & Slavin, P.A.

(57) ABSTRACT

The invention describes a foil of polymeric material comprising a plurality of patch portions and a grid portion arranged between said patches. Each patch portion is connected to the grid portion by means of one or more connecting elements. Each patch portion is separated from the grid portion in the X-Y plane by means of a release portion, said release portion having a tensile strength in the X-Y plane which is lower than the tensile strength of both said patch portions and said grid portion, such that—upon exertion of a tensile force between said patch portions and said grid portion—said foil ruptures preferentially at said release portion. The invention relates to a method for the production of cell-capture chips using said foil, and a cell capture chip produced by said method.

11 Claims, 5 Drawing Sheets

(52) U.S. Cl.
CPC .. *B01L 3/502792* (2013.01); *G01N 33/48728* (2013.01); *B01L 2200/12* (2013.01); *B01L 2300/044* (2013.01); *B01L 2300/0819* (2013.01); *B01L 2400/0638* (2013.01)

(56) References Cited

FOREIGN PATENT DOCUMENTS

| | | |
|---|---|---|
| EP | 2107040 | 10/2009 |
| WO | WO02059597 | 8/2002 |
| WO | WO03093494 | 11/2003 |
| WO | WO2005115622 | 12/2005 |
| WO | WO2006071696 | 7/2006 |

\* cited by examiner

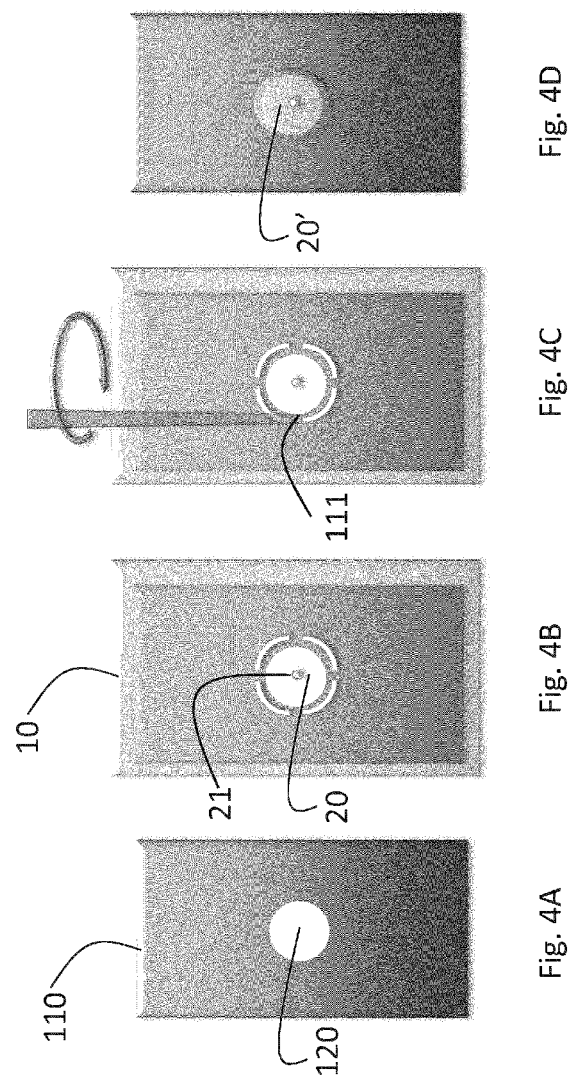

INTEGRATED POLYMER FOIL, PATCH-CLAMP ARRAY AND MEMBRANE VALVES

CROSS REFERENCE TO RELATED APPLICATIONS

This is a national stage filing in accordance with 35 U.S.C. § of PCT/EP2015/053893, filed Feb. 25, 2015, which claims the benefit of the priority of European Patent Application No. 14156499.7, filed Feb. 25, 2014, the contents of each are incorporated herein by reference.

FIELD OF THE INVENTION

The present invention relates to the field of cell-capture chips, particularly for patch clamp measurement. The invention provides manufacturing methods for such chips and components for use in said method.

BACKGROUND OF THE INVENTION

The integration of sensor chips in carrier plates, also referred to as microtitre plates, is of particular concern of the present invention. Embodiments of the chip may provide a so-called lab-on-a-chip device, which integrates laboratory functions onto a single chip. An assembly of such chips, which may comprise an array of a plurality of chips on a single carrier, is applicable in a method for determining and/or monitoring electrophysiological properties of ion channels in ion channel-containing structures, typically lipid membrane-containing structures such as cells, by establishing an electrophysiological measuring configuration in which a cell membrane forms a high resistive seal around a measuring electrode, making it possible to determine and monitor a current flow through the cell membrane. The chip is for example useful in a method for analysing the electrophysiological properties of a cell membrane comprising a glycocalyx. The chip may be used in or form part of an apparatus for studying electrical events in cell membranes, such as an apparatus for carrying out patch clamp techniques utilised to study ion transfer channels in biological membranes. In particular, with chips to be used in patch clamp techniques, good adhesion of the cell to the chip is required, so that a high-resistance seal can be obtained between the chip and the cell membrane (a "gigaseal").

A particular goal in this field has been cheap, disposable chips fabricated of polymeric material, instead of glass or silicon. However, the mechanical properties of polymeric materials are different to those of such materials, and polymeric materials are often not particularly suited to the manufacturing processes used for glass or silicon materials. In addition, polymeric material with a sufficiently high surface smoothness for establishing giga-seals has proven hard to obtain.

WO 03/093494 discloses a biochip for patch clamp detection. U.S. Pat. No. 6,899,800 describes a polymeric electrode for obtaining a gigaohm seal. WO02/059597 discloses a tight electrical seal between a cell and a surface. A mechanically compressible insulating layer is present on the carrier, which compensates for any debris trapped between the cell and the surface.

Manufacturing of chips has required time-consuming and expensive manufacturing techniques (due to the requirements of quality, cleanliness and small-scale for such devices). The present invention aims to overcome problems associated with known processes. In particular, the invention provides improved method for manufacturing of chips comprising polymeric material. In the present invention, macro-dimensional techniques and devices are used to manipulate nano-dimensional articles.

SUMMARY OF THE INVENTION

It has been found by the present inventor(s) that macro-dimensional techniques and devices can be used to manipulate nano-dimensional articles.

So, in a first aspect the present invention relates to a foil (10) of polymeric material, said foil (10) extending in an X-Y plane and having a thickness z in a direction Z perpendicular to said X-Y plane, said foil (10) comprising:
  a. a plurality of patch portions (20) of said polymeric material, arranged in a regular array in said X-Y plane, each patch portion (20) extending in said X-Y plane and having a thickness z in a direction Z perpendicular to said X-Y plane,
  b. a grid portion (30) of said polymeric material, said grid portion (30) arranged between said patches (20) in said X-Y plane and having a thickness z in a direction Z perpendicular to said X-Y plane,
wherein each patch portion (20) is connected to said grid portion (30) in said X-Y plane by means of a release portion (40), said release portion (40) having a tensile strength in the X-Y plane which is lower than the tensile strength of both said patch portions (20) and said grid portion (30), such that—upon exertion of a tensile force between said patch portions (20) and said grid portion (30)—said foil (10) ruptures preferentially at said release portion (40).

The invention also provides a method for the manufacture of a microfluidic cell-capture chip (100), said method comprising the steps of:
  a. providing a substrate (110) extending in an X-Y plane and having a thickness z1 in a direction Z perpendicular to said X-Y plane; said substrate (110) comprising a regular array of through-holes (120) in said X-Y plane;
  b. providing a foil (10) according to any one of claims 1-11;
wherein each of said through-holes (120) in said substrate (110) has a surface area in the X-Y plane which is smaller than the surface area of each patch portion (20) of said foil (10) in the X-Y plane, and wherein the array of through-holes (120) is such that each through-hole (120) of the substrate (110) aligns with and is covered by one patch portion (20) of said foil (10)
  c. forming at least one patch-hole (21) in each patch portion (20) of said foil (10),
  d. overlaying the substrate (110) with the foil (10) such that each through-hole (120) of the substrate (110) aligns with and is covered by one patch portion (20) of the foil (10);
  e. sealing each patch portion (20) to the substrate (110) in a continuous seal (111) about the periphery of each through-hole (120);
  f. removing the grid portion (30) from the substrate (110) in a manner such that the release portions (40) about each patch portion (20) rupture and one patch (20') remains sealed to the substrate (110) about each through-hole (120).
wherein step c. can take place at any point after step b.

The invention also provides a microfluidic cell-capture chip (100), said chip (100) comprising a substrate (110) extending in an X-Y plane and having a thickness z1 in a direction Z perpendicular to said X-Y plane; said substrate (110) comprising a regular array of through-holes (120) in said X-Y plane; wherein each through-hole (120) of the substrate (110) aligns with and is covered by one patch (20') of a polymeric material, wherein each patch (20') is sealed to the substrate (110) about the through-hole (120) with a continuous seal (111) and wherein the periphery of each patch (20') of polymeric material comprises one or more tags (22) of polymeric material, each patch (20') comprising at least one patch-hole (21).

Further details of the invention are apparent from the dependent claims and the following specification and figures.

LEGENDS TO THE FIGURES

The invention will be described with reference to the enclosed schematic figures, in which:

FIGS. 4A-4D show the steps of the method of the invention, with focus on one patch portion.

DETAILED DISCLOSURE OF THE INVENTION

Foil

Figure 1:
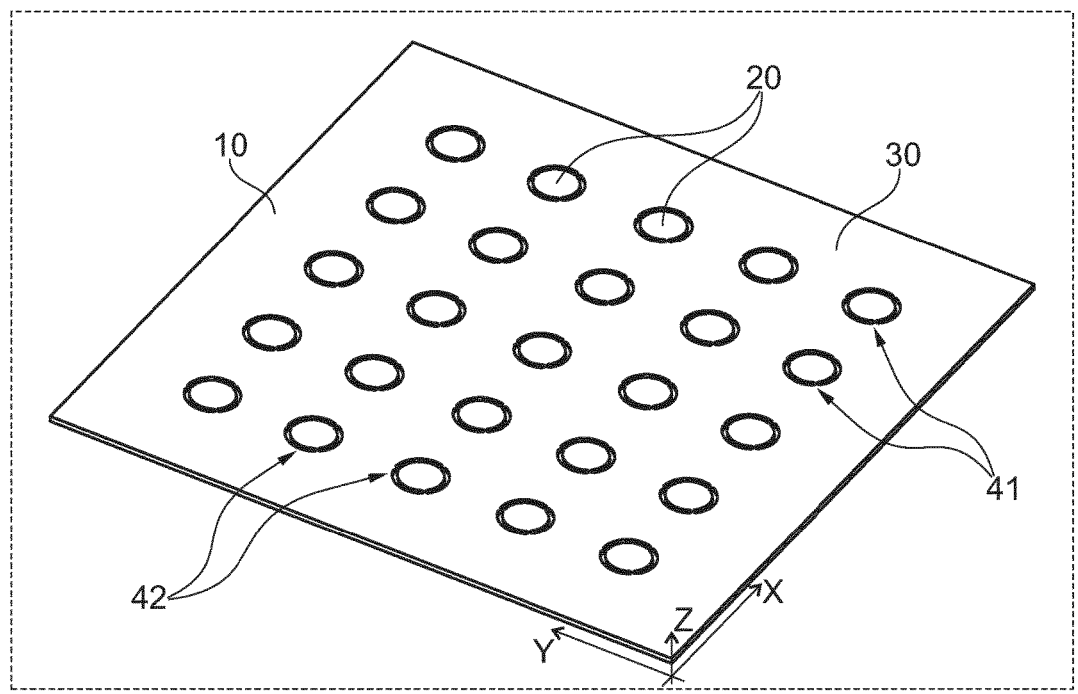
FIG. 1 shows a three-dimensional illustration of a foil according to the invention, in which the circular patch portions are arranged in a 5×5 square array.

As illustrated in FIG. 1, the invention provides a foil 10 of polymeric material. By the term "foil" is meant a material which has two major dimensions in a plane, and a much smaller dimension perpendicular to said plane. The terms "foil" and "film" may be used interchangeably. The foil 10 extends in an X-Y plane and has a thickness z (not shown in FIG. 1) in a direction Z perpendicular to said X-Y plane. The thickness z of the polymeric foil 10 is suitably between 1 and 750 µm. The extension in the X-Y plane is less important, and is suitably of a dimensions between 10 mm to 1000 mm in both X and Y.

The foil 10 is made of a polymeric material, and preferably has a substantially uniform density and thickness throughout its extension in the X-Y plane. Preferred polymeric materials for the foil 10 include polycarbonate (PC), polyamide (PA), polyimide (PI), Liquid Crystal Polymer (LCP), polysulfone (PSU), polyethyleneimine (PEI), polyphenylsulfide (PPS), polyethylene teraphthalate (PET), polypropylene, polyethylene (PE), as well as co-polymers, block copolymers and blends thereof. Most preferred polymers are polycarbonate, polyamide, polystyrene and polyethylene teraphthalate.

All portions of the foil 10 (patch portions 20, grid portion 30 and release portions 40) are separate, connected portions of the foil 10, and are made of the same polymeric material.

As can be seen in FIG. 1, the foil 10 comprises a plurality of patch portions 20 of said polymeric material, arranged in a regular array in said X-Y plane. Suitably, the regular array is a square array, in which patch portions 20 are arranged in perpendicular straight lines, as per the 5×5 array shown in FIG. 1.

For maximum efficiency of the method of the invention, each foil 10 suitably comprises at least 10 patch portions 20, such as at least 20 patch portions. Each patch portion 20 extends in the X-Y plane and has a thickness z in a direction Z perpendicular to said X-Y plane.

Each patch portion 20 has a geometrically regular form in the X-Y plane, e.g. a circular form. FIGS. 3A-3H illustrate square (3A, 3C, 3E and 3G) and circular (FIGS. 3B, 3D, 3F, 3H) patch portions. Geometrically regular forms for the patch portions 20 are not required, as long as there is sufficient weakening of the foil in the z-axis to facilitate tearing.

The foil 10 shown in FIG. 1 also comprises a grid portion 30 of polymeric material. The grid portion 30 is the continuous portion of the foil 10 which extends between the patch portions 20 and connects them in the foil 10. Suitably, the foil 10 consists solely of a plurality of patch portions 20 and a grid portion 30; i.e. the grid portion 30 comprises the remainder of the foil 10 between said patch portions 20.

The grid portion 30 is therefore arranged between said patch portions 20 in said X-Y plane and has a thickness z in a direction Z perpendicular to said X-Y plane.

Each patch portion 20 is connected to the grid portion 30 in said X-Y plane by means of a release portion 40. Suitably, the periphery of each patch portion 20 is defined in said X-Y plane by the release portion 40. The release portion 40 has a tensile strength in the X-Y plane which is lower than the tensile strength of both said patch portions 20 and said grid portion 30, such that—upon exertion of a tensile force between said patch portion 20 and said grid portion 30—said foil 10 ruptures preferentially at said release portion 40. In other words, upon application of a tensile force to the foil 10, the release portion 40 acts to release patch portions 20 from said grid portion 30.

The release portion 40 may take a number of forms. In one aspect, the release portion 40 comprises a portion of said foil 10 which is thinner than each of said patch portions 20 and/or said grid portion 30. Upon application of a tensile force, the release portion 40 stretches and ruptures. A foil 10 comprising thin release portions 40 may be made by designing a mould being shallower at the release portions 40 or by mechanically stretching or removing foil material at the release portions 40.

In another aspect, the release portions 40 comprises a portion of said foil 10 which has been irradiated such that it becomes weaker than the surrounding patch portions 20 and grid portion 30.

Figure 2:
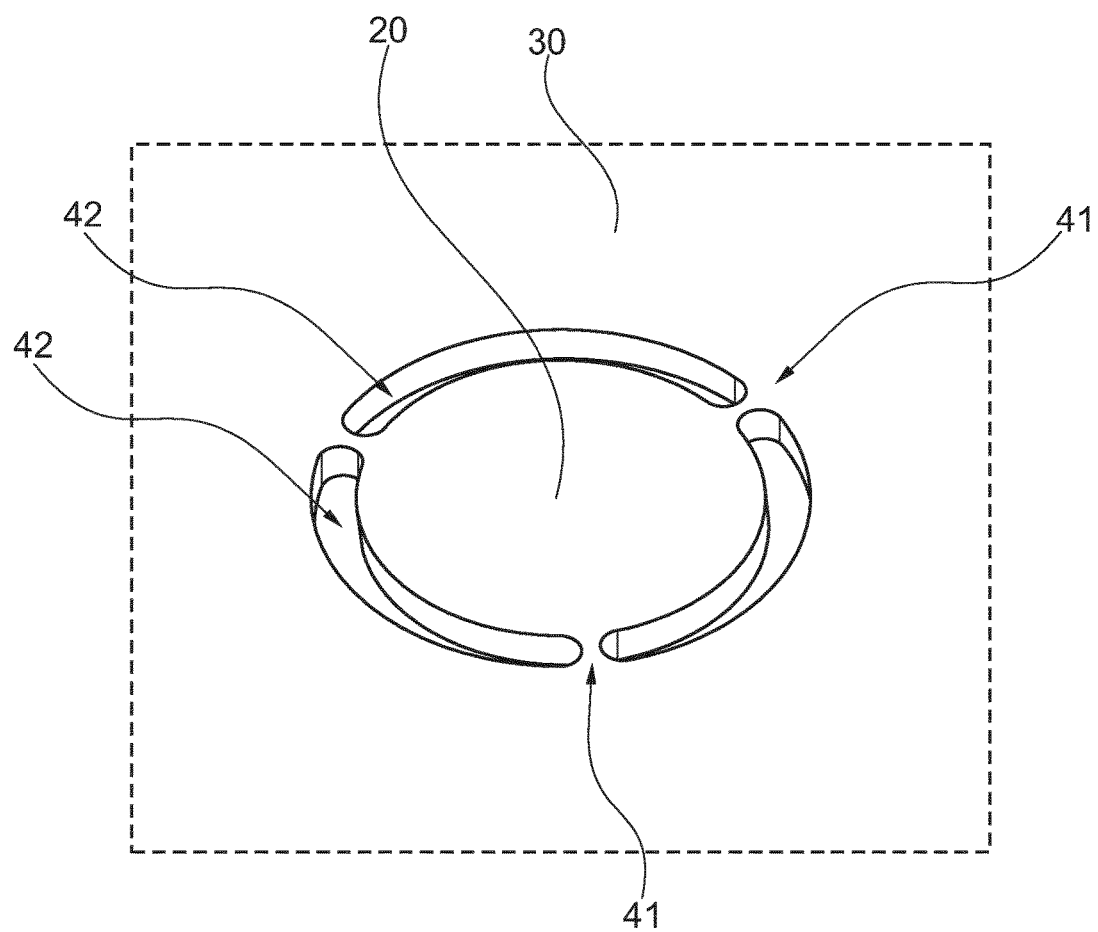
FIG. 2 is a close- up of one of the patch portions of FIG. 1

As illustrated in detail in FIG. 2, each release portion 40 may comprise one or more connecting elements 41. Connecting elements 41 extend from the edge of each patch portion 20 in the X-Y plane and connect it to the grid portion 30. Connecting elements 41 are made of the same polymeric material as the foil 10. Typically, there are two or more, three or more, such as e.g. 3, 4, 5, 6, 7, 8, 9 or 10 connecting elements 41 per patch portion 20.

In this aspect, each release portion 40 also comprises one or more connecting elements 42. Each patch portion 20 is separated from the grid portion 30 in the X-Y plane by means of one or more cut-out regions 42. The cut-out regions 42 are regions of the foil 10 in which the polymeric material has been removed, to provide cut-out regions extending through the thickness of the polymer foil 10. Together, the cut-out regions 42 and the connecting elements 41 define the release portion 40. To ensure that the connecting elements 41 can rupture as required during use of the foil 10, the connecting elements 41 should be relatively thin. To ensure this, according to the invention, the one or more cut-out regions 42 together define at least 60% of the perimeter of each patch region 20 in the X-Y plane. That is, if the perimeter of each patch region 20 is measured in the X-Y plane, more than 60% of this distance will be defined by cut-out regions 42. As per the illustrated embodiments, cut-out regions 42 may together define at least 70%, preferably at least 80%, more preferably at least 90%, most preferably about 95% of the perimeter of each patch portion 20 in the X-Y plane.

Typically, there are two or more, three or more, such as e.g. 3, 4, 5, 6, 7, 8, 9 or 10 cut-out regions 42 per patch portion 20. The number of cut-out regions 42 is usually the same as the number of connecting regions 41, and—for ease of manufacture and mechanical stability of the foil 10—is typically at least 2, such as e.g. 3 or 4.

Cut-out regions 42 typically take the form of arcs, circles, parallelograms or other such forms, as illustrated in FIGS. 3A-3H. Suitably, the connecting elements 41 are arranged equidistantly about the perimeter of each patch portion 20 in the X-Y plane. In FIGS. 3A-3H, cut-out regions 42 are marked as black areas, and connecting elements 41 occupy the regions between adjacent cut-out regions 42. The labelling of FIGS. 3B-3H has been omitted for clarity, but is the same as FIG. 3A.

Figure 3A:
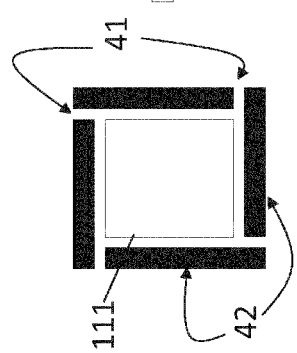
FIG. 3a-3h illustrate various patch portions according to the invention.
Figure 3B:
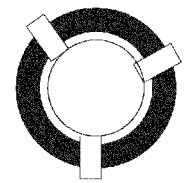
Figure 3C:
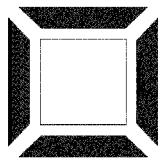
Figure 3D:
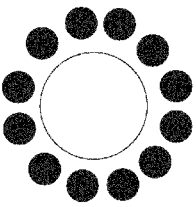
Figure 3E:
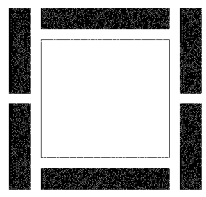
Figure 3F:
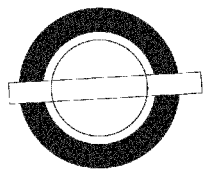
Figure 3G:
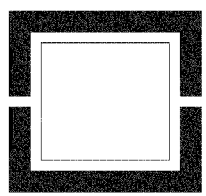
Figure 3H:
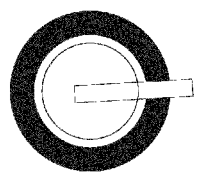

FIGS. 3A and 3C illustrate embodiments having 4 connecting elements 41 and 4 cut-out regions 42 about a square patch region 20. FIG. 3B illustrates an embodiment having 3 connecting elements 41 and 3 cut-out regions 42 about a circular patch region 20. FIG. 3D illustrates an embodiment having 13 connecting elements 41 and 13 cut-out regions 42 about a circular patch region 20 (=perforated design). FIG. 3E illustrates an embodiment having 6 connecting elements 41 and 6 cut-out regions 42 about a square patch region 20. FIG. 3F illustrates an embodiment having 2 connecting elements 41 and 2 cut-out regions 42 about a circular patch region 20. FIG. 3G illustrates an embodiment having 2 connecting elements 41 and 2 cut-out regions 42 about a square patch region 20. FIG. 3H illustrates an embodiment having 1 connecting element 41 and 1 cut-out region 42 about a circular patch region 20. The skilled person will be able to develop variants of the connecting elements 41 and cut-out regions 42 other than those shown in FIG. 3A-3H, while remaining within the scope of the present invention.

Combinations of the above methods for forming release portions 40 may be used within the same foil 10, and even within one patch region 20. That is, a release portion 40 may e.g. comprise cut-out regions 42 and connecting regions 51, and—at the same time—be thinner than each of said patch portions 20 and/or said grid portion 30.

The foil 10 illustrated in FIG. 2 is typically manufactured by forming cut-out regions 42 in a single continuous foil, thus defining patch regions 20, grid region 30 and connecting elements 41. Cut-out regions 42 are typically formed by laser cutting of the foil 10, which is a relatively clean process capable of ablating very fine structures with high precision. Stamping out and machining are alternative processes for forming cut-out regions 42.

The foil 10 preferably comprises at least one patch-hole 21' located in each patch region 20 (not illustrated in FIGS. 1-2). The patch-hole 21' is located centrally on said patch region 20. Suitably, one patch-hole 21' located in each patch region 20.

Method

The invention also provides a method for the manufacture of a microfluidic cell-capture chip 100. The method is illustrated schematically in FIGS. 4A-4D, with focus on a single patch region 20.

The first step in the method of the invention is the provision of a substrate 110 (FIG. 4A). The substrate 110 constitutes the base of the cell-capture chip 100, and provides strength and rigidity to the chip 100. The substrate 110 extends in an X-Y plane and has a thickness z1 in a direction Z perpendicular to said X-Y plane. The substrate 110 typically has a thickness of 10-10000 μm. The dimensions of the substrate 110 in the X-Y plane may be substantially the same as those of the foil 10.

The substrate 110 comprises a regular array of through-holes 120 in said X-Y plane. FIG. 4A illustrates one through-hole 120. The through-holes are typically circular, and are suitably 50 μm or larger in diameter, typically in the order of 100-300 μm in diameter. Through-holes may be though-drilled using mechanical drills. Holes may also be drilled by laser ablation depending on material and thickness. The substrate 110 typically includes additional components such as electrodes and electrical connectors. Such electrodes and electrical connectors may be formed by screen printing (thick film electrodes), physical vapour deposition of thin films, or electrolessly plated electrodes.

Typically, the substrate 110 is made of a polymeric material. Polymeric materials suitable for use in the substrate 110 include polycarbonate (PC), polyamide (PA), polyimide (PI), Liquid Crystal Polymer (LCP), polysulfone (PSU), polyethyleneimine (PEI), polyphenylsulfide (PPS), polyethylene teraphthalate (PET), polypropylene, polyethylene (PE), as well as co-polymers, block copolymers and blends thereof. Most preferred polymers for the substrate are polycarbonate, polyamide, polystyrene and polyethylene terephthalate. Dopants or materials with a lower glass transition temperature (Tg) may be included for enhancement of the bonding with the film 10. It is possible that the polymeric material used for the substrate 110 and the film 10 is the same. However, in one interesting aspect, it is useful to "mismatch" the materials of the film 10 and substrate 110; i.e. that the polymeric material of the substrate 110 is not the same as the polymeric material of the film 10. For instance, the tendency of cells to migrate or settle at the patches 20' rather than on the substrate 110 may be promoted by variation in relative properties (e.g. electrostatic properties, hydrophilic/hydrophobic properties) of the polymeric materials making up these components.

The method of the invention also requires providing a foil 10 as defined above (see FIG. 4B). At least one patch-hole 21 is formed in each patch portion 20. Preferably, only one patch-hole 21 is formed in each patch portion 20. Patch-holes 21 are suitably located centrally on each patch portion 20.

The foil 10 and substrate 110 are selected to be complementary. Accordingly, each of said through-holes 120 in said substrate 110 has a surface area in the X-Y plane which is smaller than the surface area of each patch portion 20 of said foil 10 in the X-Y plane. Additionally, the array of through-holes 120 in the substrate 110 matches the array of patch regions 20 in the foil 10. This means that—when the foil 10 and substrate 110 are overlaid—each through-hole 120 of the substrate 110 aligns with and is covered by one patch portion 20 of said foil 10 (as per FIG. 4B).

The substrate 110 is overlaid with the foil 10 such that each through-hole 120 of the substrate 110 aligns with and is covered by one patch portion 20 of the foil 10 (FIG. 4B). As can be seen, the patch portion 20 completely covers the through-hole 120 in FIG. 4B.

Once the substrate 110 and foil 10 are in place, each patch portion 20 is sealed to the substrate 110 in a continuous seal 111 about the periphery of each through-hole 120 (FIG. 4C).

The continuous seal 111 which seals each patch portion 20 to the substrate 110 typically takes place by laser welding, and is also visible in FIGS. 3A-3H (line 111). The continuous seal does not necessarily have the same shape as the patch portion 20 in the X-Y plane, but this is advantageous for the most effective use of polymeric material.

After sealing each patch portion 20 to the substrate 110 as described, the grid portion 30 of the foil 10 is removed from the substrate 110 in a manner such that the release portions 40 about each patch portion 20 rupture (FIG. 4D). In the particular aspect in which the release portion 40 comprises cut-out regions 42 and connecting elements 41, the connecting elements act 41 as sacrificial elements, and are torn during this step. The grid portion 30 of the foil 10 is completely removed from the substrate 110. One patch 20' remains sealed to the substrate 110 about each through-hole 120.

The step of forming patch-holes 21 can take place in theory at any point during the method; however, it is preferred that patch-holes 21 are formed in the foil 10 before the foil 10 and substrate 110 are overlaid.

If there are processes such as surface modification of the substrate 110, the foil 10 can also remain entirely or partly in place until such steps are carried out. As such, the residual foil 10 can form a natural mask to prevent unintended areas being coated.

The use of the foil 10 in this manner provides an easy way to obtain fine, accurate patch-holes (in the relatively thin foil 10) while maintaining sufficient structural support (by means of the substrate 110). It is not possible to simply form patch-holes 21 of the desired accuracy and quality in substrates as thick as those used in the present invention. In addition, the inventors have attempted to manually seal individual patches 20' to an array of through-holes 120 in a substrate 110 without success. The "tear-off" method of the invention provides great benefit in that macro-dimensional techniques and devices are used to manipulate nano-dimensional articles.

Cell-Capture Chip

The invention also provides a microfluidic cell-capture chip 100, which is obtainable via the method of the invention. The materials of the various components of the chip 100 are as described above.

The chip 100 comprises a substrate 110 extending in an X-Y plane and having a thickness z1 in a direction Z perpendicular to said X-Y plane. The substrate 110 typically has a thickness z1 of 10-10000 µm.

The substrate 110 comprises a regular array of through-holes 120 in said X-Y plane, as described above. Suitably, the regular array is a square array, in which through-holes 120 are arranged in perpendicular straight lines. The substrate 110 suitably comprises at least 10 through-holes 120, such as at least 20 through-holes 120.

Each through-hole 120 of the substrate 110 aligns with and is covered by one patch 20' of a polymeric material. Each patch 20' is sealed to the substrate 110 about the through-hole with a continuous seal 111. Sealing may take place via any of the methods described above, but is preferably laser welding, for reasons of efficiency and accuracy. Each patch 20' corresponds to a patch region 20 in the method of the invention.

Figure 5A:
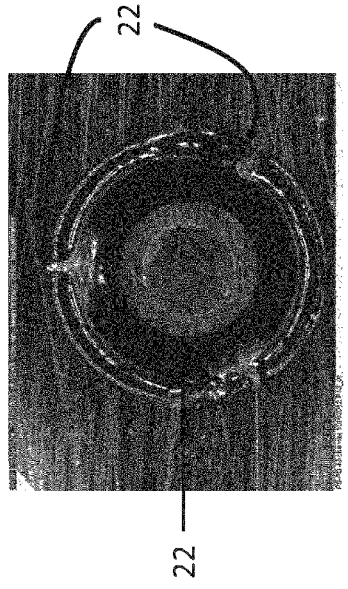
FIGS. 5a-5c are photographs of laser welded cell-capture chips, with images clearly showing "tags" about the periphery of each patch.
Figure 5B:
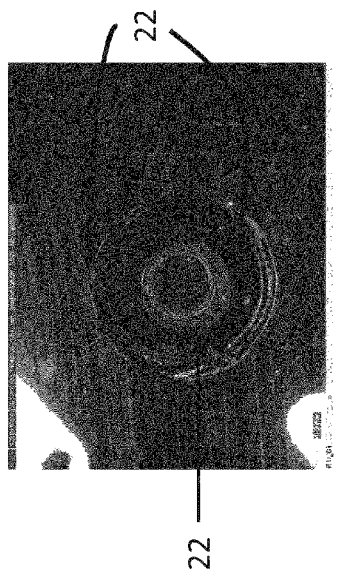
Figure 5C:
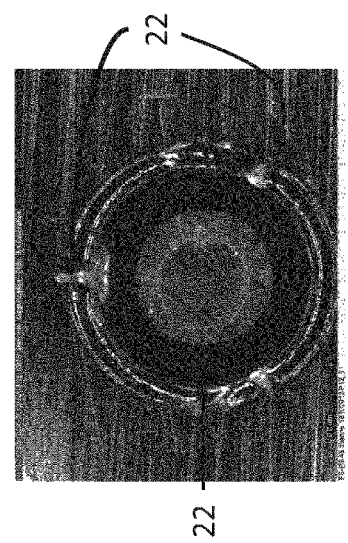

The periphery of each patch 20' (in the X-Y plane) of polymeric material comprises one or more tags 22 of polymeric material. The tags 22 are remnants of the connecting elements 40, after having been torn from the grid region 30 in the method of the invention. In other words, the periphery of each patch 20' is not entirely smooth, but comprises irregularities. FIGS. 5a-5c are photographs of laser welded cell-capture chips, with images clearly showing tags 22 about the periphery of each patch 20'.

As the tags 22 originate from the connecting elements 40, there are typically two or more, three or more, such as e.g. 3, 4, 5, 6, 7, 8, 9 or 10 tags 22 per patch 20'. Tags 22 are suitably arranged equidistantly about the perimeter of each patch 20' in the X-Y plane. The tags 32 occupy a relatively small portion of total perimeter of the patch 20'; i.e. less than 40% of the perimeter, less than 30%, less than 20%, less than 10% of the total perimeter of the patch 20'.

Each patch 20' of the cell-capture chip 110 comprises at least one patch-hole 21. By applying a pressure differential across the patch-hole 21, biological cells can be trapped at the patch hole 21 and patch-clamp experiments can be carried out.

Patches 20' and patch portions 20 are typically circular, and have a diameter of between 50 and 1000 µm, preferably between 100 and 500 µm. Patch holes 21 are also typically circular.

Flexing Membrane Valve Element

The invention also provides a flexing membrane valve element, and method for making such a valve element. The valve element is similar does not include the patch holes 21 which are present in the cell-capture chip 100, but is otherwise identical.

The invention thus provides a flexing membrane valve element (200), said valve element (200) comprising a substrate (210) extending in an X-Y plane and having a thickness z1 in a direction Z perpendicular to said X-Y plane; said substrate (210) comprising a regular array of through-holes (220) in said X-Y plane; wherein each through-hole (220) of the substrate (210) aligns with and is covered by one patch (20') of a polymeric material, wherein each patch (20') is sealed to the substrate (210) about the through-hole (220) with a continuous seal (211) and wherein the periphery of each patch (20') of polymeric material comprises one or more tags (22) of polymeric material.

Similarly, the invention provides a method for the manufacture of a flexing membrane valve element (200), said method comprising the steps of:

a. providing a substrate (210) extending in an X-Y plane and having a thickness z1 in a direction Z perpendicular to said X-Y plane; said substrate (210) comprising a regular array of through-holes (220) in said X-Y plane;
b. providing a foil (10) according to the invention;
wherein each of said through-holes (220) in said substrate (210) has a surface area in the X-Y plane which is smaller than the surface area of each patch portion (20) of said foil (10) in the X-Y plane, and wherein the array of through-holes (220) is such that each through-hole (220) of the substrate (110) aligns with and is covered by one patch portion (20) of said foil (10)
c. overlaying the substrate (210) with the foil (10) such that each through-hole (220) of the substrate (210) aligns with and is covered by one patch portion (20) of the foil (10);
d. sealing each patch portion (20) to the substrate (210) in a continuous seal (211) about the periphery of each through-hole (220);
e. removing the grid portion (30) from the substrate (210) in a manner such that the release portions (40) about each patch portion (20) rupture and one patch (20') remains sealed to the substrate (210) about each through-hole (220).

EXAMPLE 1

Commercially available foils (20-100 um) are have segments cut out then patch holes are drilled. Laser parameters are selected for the best performance of speed and quality. In the laser welding unit, the carrier substrate with four alignment holes is placed on the laser welding fixture with matching alignment pins. The foil is blown off with compressed air to remove debris then is placed on top of the carrier substrate/laser welding fixture. A quartz glass compression plate is used to ensure maximum contact between foil and substrate. Laser welding is then performed. The welded part is removed from the fixture with specified areas of welded foil, in this case, within the cut-out circumference completely, and covering the first third of the cut-out tabs (release portions). At this point, quality control, (visual, liquid or other) is done. If other surface coatings are done (glass, PTFE type coatings, low drug adsorption coatings for drug discovery), then the foil proceeds to these processes. In the final step, the bulk of the foil material is removed (mechanically) and separation occurs around the circumference of the weld area at the weakened, cut out areas.

The invention claimed is:

1. A method for the manufacture of a microfluidic cell-capture chip (100), said method comprising the steps of:
   a. providing a substrate (110) extending in an X-Y plane and having a thickness zl in a direction Z perpendicular to said X-Y plane; said substrate (110) comprising a regular array of through-holes (120) in said X-Y plane;
   b. providing a foil (10) of polymeric material, said foil (10) extending in an X-Y plane and having a thickness z in a direction Z perpendicular to said X-Y plane, said foil (10) comprising:
      i. a plurality of patch portions (20) of said polymeric material, arranged in a regular array in said X-Y plane, each patch portion (20) extending in said X-Y plane and having a thickness z in a direction Z perpendicular to said X-Y plane,
      ii. a grid portion (30) of said polymeric material, said grid portion (30) arranged between said patches (20) in said X-Y plane and having a thickness z in a direction Z perpendicular to said X-Y plane,
      wherein each patch portion (20) is connected to said grid portion (30) in said X-Y plane by a release portion (40), said release portion (40) having a tensile strength in the X-Y plane which is lower than the tensile strength of both said patch portions (20) and said grid portion (30), such that upon exertion of a tensile force between said patch portions (20) and said grid portion (30) said foil (10) ruptures preferentially at said release portion (40);
   wherein each of said through-holes (120) in said substrate (110) has a surface area in the X-Y plane which is smaller than the surface area of each patch portion (20) of said foil (10) in the X-Y plane, and wherein the array of through-holes (120) is such that each through-hole (120) of the substrate (110) aligns with and is covered by one patch portion (20) of said foil (10);
   c. forming at least one patch-hole (21) in each patch portion (20) of said foil (10);
   d. overlaying the substrate (110) with the foil (10) such that each through-hole (120) of the substrate (110) aligns with and is covered by one patch portion (20) of the foil (10);
   e. sealing each patch portion (20) to the substrate (110) in a continuous seal (111) about the periphery of each through-hole (120);
   f. removing the grid portion (30) from the substrate (110) in a manner such that the release portions (40) about each patch portion (20) rupture and one patch (20') remains sealed to the substrate (110) about each through-hole (120);
   wherein step c. can take place at any point after step b.

2. A method for the manufacture of a microfluidic cell-capture chip according to claim 1, wherein the periphery of each patch portion (20) is defined in said X-Y plane by said release portion (40).

3. A method for the manufacture of a microfluidic cell-capture chip according to claim 1, wherein each patch portion (20) has a geometrically regular form in the X-Y plane, e.g. a circular form.

4. A method for the manufacture of a microfluidic cell-capture chip according to claim 1, wherein said grid portion (30) comprises the remainder of the foil (10) between said patch portions (20).

5. A method for the manufacture of a microfluidic cell-capture chip according to claim 1, wherein each release portion (40) comprises a portion of said foil (10) which is thinner than each of said patch portions (20) and/or said grid portion (30).

6. A method for the manufacture of a microfluidic cell-capture chip according to claim 1, wherein each release portion (40) comprises one or more connecting elements (41) connecting said patch portion (20) to said grid portion (30) in the X-Y plane, and one or more cut-out regions (42) extending through the thickness of the polymer foil (10), said cut-out regions (42) separating each patch portion (20) from said grid portion (30) in the X-Y plane, wherein said one or more cut-out regions (50) together define at least 60% of the perimeter of each patch portion (20) in the X-Y plane.

7. A method for the manufacture of a microfluidic cell-capture chip according to claim 1, wherein said cut-out regions (42) together define at least 70% of the perimeter of each patch portion (20) in the X-Y plane.

8. A method for the manufacture of a microfluidic cell-capture chip according to claim 1, wherein each release portion (40) comprises two or more cut-out regions (42).

9. A method for the manufacture of a microfluidic cell-capture chip according to claim 1, wherein the connecting elements (41) are arranged equidistantly about the perimeter of each patch portion (20) in the X-Y plane.

10. A method for the manufacture of a microfluidic cell-capture chip according to claim 1, wherein patch portions (20) are typically circular, and have a diameter of between 50 and 1000 μm.

11. The method for the manufacture of a microfluidic cell-capture chip (100) according to claim 1 wherein the step of forming at least one patch-hole (21) in each patch portion (20) of said foil (10) occurs after the step of overlaying the substrate (110) with the foil (10).

* * * * *